(12) United States Patent
French et al.

(10) Patent No.: US 8,948,581 B2
(45) Date of Patent: *Feb. 3, 2015

(54) PATIENT INFUSION MEDIA WARMER AND METHOD OF USE

(71) Applicant: Thermacore Technologies, Inc., Dallas, TX (US)

(72) Inventors: C. Kenneth French, Cranfills Gap, TX (US); Garrett Barker, Meridian, TX (US); Wyatt Earp, Los Angeles, CA (US)

(73) Assignee: Thermacore Technologies, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/900,326

(22) Filed: May 22, 2013

(65) Prior Publication Data

US 2013/0252190 A1    Sep. 26, 2013

Related U.S. Application Data

(63) Continuation of application No. 11/501,238, filed on Aug. 9, 2006, now Pat. No. 8,467,671.

(60) Provisional application No. 60/773,314, filed on Feb. 15, 2006, provisional application No. 60/773,336, filed on Feb. 15, 2006, provisional application No. 60/707,182, filed on Aug. 11, 2005.

(51) Int. Cl.
*A61F 7/00* (2006.01)
*A61M 5/44* (2006.01)
*H05B 3/26* (2006.01)
*H05B 3/28* (2006.01)

(52) U.S. Cl.
CPC ............... *A61M 5/44* (2013.01); *H05B 3/267* (2013.01); *H05B 3/286* (2013.01); *A61M 2205/3368* (2013.01); *A61M 2205/3653* (2013.01); *H05B 2203/003* (2013.01); *H05B 2203/036* (2013.01)
USPC ............ 392/470; 392/465; 604/113; 604/114

(58) Field of Classification Search
None
See application file for complete search history.

(56) References Cited

U.S. PATENT DOCUMENTS

| | | | |
|---|---|---|---|
| 4,680,445 A | 7/1987 | Ogawa | |
| 5,211,849 A | 5/1993 | Kitaevich et al. | |
| 5,245,693 A | 9/1993 | Ford et al. | |
| 5,254,094 A | 10/1993 | Starkey et al. | |
| 6,175,688 B1 | 1/2001 | Cassidy et al. | |
| 6,480,257 B2 | 11/2002 | Cassidy et al. | |
| 6,629,946 B2 | 10/2003 | Fressinet et al. | |
| 6,641,556 B1 * | 11/2003 | Shigezawa | 604/113 |
| 6,824,528 B1 | 11/2004 | Faries, Jr. et al. | |
| 8,467,671 B2 * | 6/2013 | French et al. | 392/470 |

* cited by examiner

*Primary Examiner* — Thor Campbell
(74) *Attorney, Agent, or Firm* — Arent Fox LLP

(57) ABSTRACT

A warming unit and method for warming an infusion medium prior to introducing the medium into a patient's body. The apparatus includes an outer casing, inlet and outlet tubes secured to the outer casing, a fluid conduit for transporting the infusion medium through the warming unit, and a heating element disposed proximate to the fluid conduit for warming the infusion medium flowing therethrough. The warming unit can form part of a system, which further includes a controller for controlling various functions of and separate from the warming unit, a reservoir containing the infusion medium, and a power source for powering the warming unit.

24 Claims, 8 Drawing Sheets

PATIENT INFUSION MEDIA WARMER AND METHOD OF USE

CROSS-REFERENCE TO RELATED APPLICATIONS

This application is a continuation of U.S. application Ser. No. 11/501,238, filed Aug. 9, 2006, which claims the benefit of U.S. Provisional Application No. 60/707,182, filed Aug. 11, 2005, U.S. Provisional Application No. 60/773,336, filed Feb. 15, 2006, and U.S. Provisional Application No. 60/773,314, filed Feb. 15, 2006, each of which is incorporated herein by reference in its entirety.

BACKGROUND OF THE INVENTION

1. Field of the Invention

The present invention relates to a warming unit for warming a fluid flowing therethrough, and, in particular, to a warming unit for warming a patient infusion medium being infused into a patient. The warming unit forms part of a system for warming a patient infusion medium including, for example, a controller for controlling and monitoring various characteristics of the warming unit and a power unit for powering the system.

2. Description of Related Art

Warming systems for warming a patient infusion medium (interchangeably referred to as "medium") for infusion into a patient via an infusion tube, indirectly or directly, are known in the art. Some such systems, for example, may typically use a coiled length of tube to minimize the area necessary for contact with or placement in close proximity to an indirect heating element. Other systems use a heating element integrated with tubing, such as a braided heating element disposed between inner and outer layers of a dual extruded tube. Prior art warming systems also typically provide for measuring the temperature of the medium at some point within the system, and include a control unit integral with the heating element. Such control unit generally controls power to the heating element and measures the output temperature of the medium.

However, the warming systems of the prior art suffer from drawbacks and problems. One such problem is that the warming systems tend to be bulky and un-ergonomic, which leads to patient discomfort when the warming system is secured to the body of the patient.

A second problem with prior art warming systems is that they are prone to leakage. One source of leakage typically is the location at which a connector, or luer, at an end of the heating systems attaches to a mating connector of a neighboring piece of tubing. A second source of typical leakage is heating element overheating, which, for example, may create a hole in the tubing. This problem is compounded in those heating systems having onboard circuitry: once the infusion medium passes through the hole in the tubing, the escaped medium may contact the circuitry, and, in some cases, the heating system may short, smoke, and/or catch fire. As a result, a safety hazard can occur, the patient may be placed in discomfort or danger, and the heating system may need to be replaced. Further, any medical procedure underway might also need to be suspended while the heating system is replaced.

SUMMARY OF THE INVENTION

The present invention solves these problems, as well as others, by providing a warming unit and system for warming a patient infusion medium, wherein the warming unit includes an ergonomic design that is comfortably securable to a patient or easily attachable to another location, and provides an efficient warming operation, a low risk of leakage, and an improved flowrate over the medium warmers of the prior art. Embodiments of the present invention include separate control electronics from the warming unit, thereby reducing or eliminating problems associated with prior art integrated systems.

According to one embodiment of the present invention, the warming unit includes an outer casing, a laminated heating assembly, one or more sensors, and inlet and outlet tubes. The warming unit optionally includes a connector port for connecting the fluid warmer to a controller, which controls various functions of the fluid warmer. A fluid conduit is formed within the casing, and, according to one embodiment, the fluid conduit defines a serpentine or meandering path, prolonging a time period during which a medium passing through the warming unit is in contact with, or in close proximity to, the laminated heating assembly. Among other advantages, the conduit of some embodiments of the present invention reduces formation of air bubbles in the medium to be conducted, by sizing and/or shaping the cross-sectional area of the conduit such that bubble formation has a low likelihood of occurrence.

According to one embodiment, the laminated heating assembly includes a heating element disposed on a plate, which is sandwiched between first and second insulating sheets. The laminated heating assembly may also include one or more sensors for measuring the temperature of the heating element or the medium flowing through the warming unit, for example. Examples of sensors applicable to the present invention include, but are not limited to, thermocouples, thermistors, resistor elements, and any other suitable device for measuring and/or otherwise determining temperature. According to a further embodiment of the present invention, the heating element is located proximate to the fluid conduit and aligns with and extends along the fluid conduit in a parallel manner, although it is within the scope of the present invention that the heating element is in the form of other shapes and configurations.

The laminated heating assembly is provided within the outer casing, for example, by being enclosed between first and second portions of the outer casing. Further, the warming unit optionally includes a plurality of extensions and corresponding openings formed on the first and second casing portions, respectively, to align and secure the casing portions together. The warming unit optionally also includes a seal disposed between the first and second casing portions. The seal is seated, for example, within a groove formed in one of the first and second casing portions. The first and second casing portions may be secured together by ultrasonic welding, gluing, or any other suitable method of attachment. In some embodiments, once assembled together, the first and second casing portions are permanently secured to each other. As a result, the warming unit has improved leakage and tamper resistance. In some variations, the warming unit is intended to be disposed after a single use.

In embodiments of the present invention, the warming unit includes a connector portion formed on, for example, or otherwise attached to, the laminated heating assembly. The connector portion includes one or more contact points to provide power to the heating element and to transmit signals with the one or more sensors and/or other features of the unit. The contact points are coupled, for example, to the heating element, to the one or more sensors, and/or to other features via circuit paths formed on the laminated heating assembly or via wires or other couplings. Wires or other couplings connected to the connector portion, in turn couple the warming unit to the controller and/or a power source. In some embodiments, the power source may be attached and detached from the connector portion, allowing flexibility in portability of the warming unit and the use of a variety of power sources (e.g., any power source meeting the power requirements may be connected via the connector portion, so long as suitable connection mechanism is provided). Other features optionally included with the warming unit include a flowrate measurement device to measure a flowrate of a medium passing through the warming unit or otherwise delivered to a patient.

In some embodiments, external control circuitry for controlling the temperature of the medium flowing through the warming unit is contained in a controller. Consequently, the circuitry is not susceptible to shorting, smoking, or catching fire, for example, as a result of escaped medium from the heating unit coming into contact with the control circuitry. The warming unit of the present invention thereby provides improved patient and caregiver safety and reliability over prior art warmers having integrated control circuitry.

In some embodiments, the warming unit forms a portion of or is otherwise usable with an infusion medium warming system, which further includes, for example, a power supply, a separate controller, and a reservoir for a medium to be warmed. In some embodiments, the controller provides power or controls power delivery to, and transmits and receives data, such as inlet and outlet temperature data, with the warming unit. The controller may also receive and display a temperature of the heating element of the warming unit or display or receive input of other information. Display may include, for example, such information as a visual alarm or the temperature of the medium flowing through the warming unit (e.g., inlet and/or outlet temperature). Additionally, the controller may also include an audible and/or visual alarm, for example, which is triggered when the monitored temperature exceeds a predetermined value, or when another alarm condition exists.

Additional advantages and novel features of the invention will be partially set forth in the description that follows, and will also become apparent to those skilled in the art upon examination of the following or upon learning by practice of the invention.

BRIEF DESCRIPTION OF DRAWINGS

Other aspects of the present invention will be better understood from the following description, along with the accompanying drawings, wherein.

DETAILED DESCRIPTION

Figure 1:
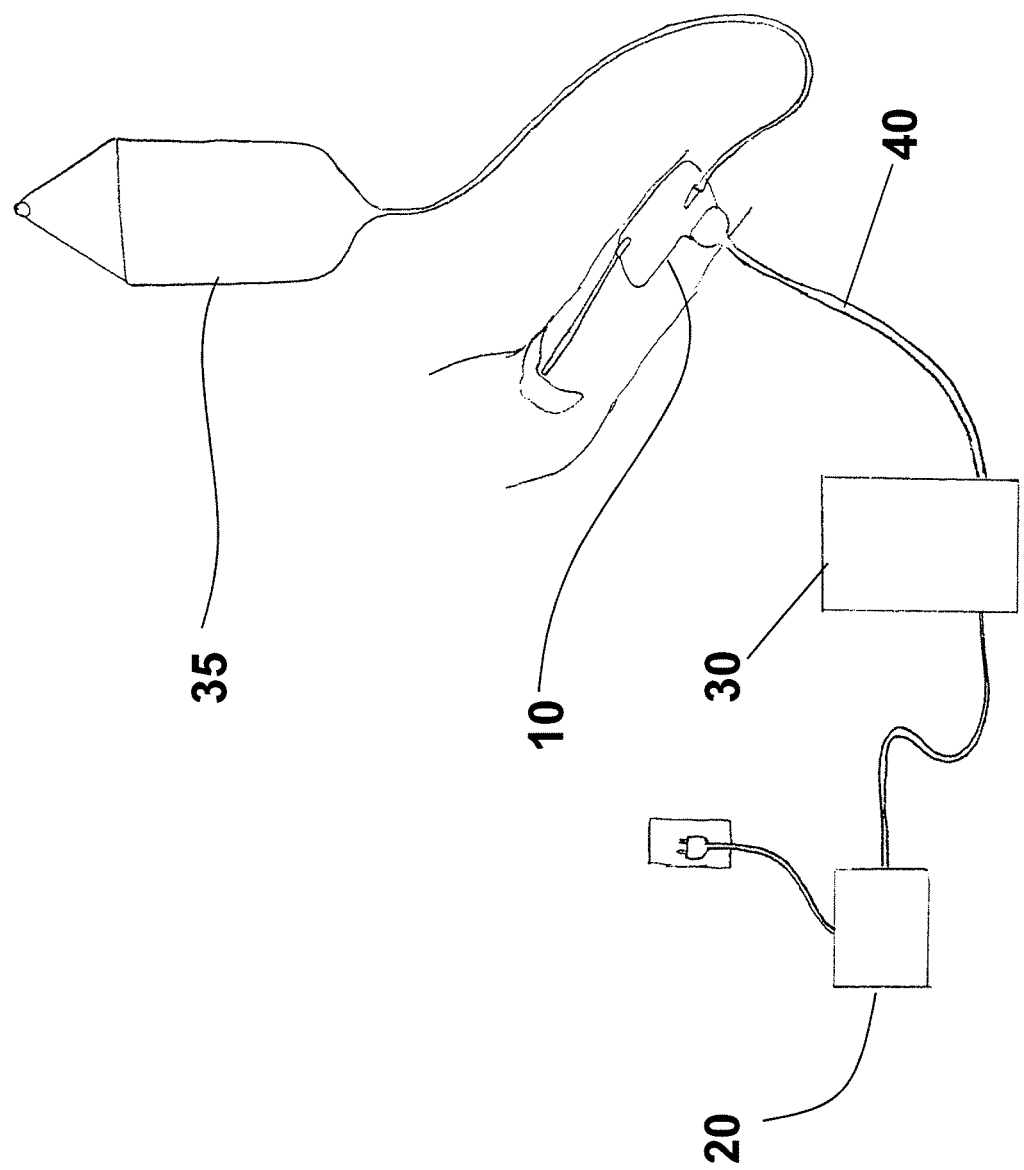
FIG. 1 shows an infusion medium warming system, including a medium reservoir, a warming unit, a controller for monitoring and controlling the warming unit, and a power supply, in accordance with an embodiment of the present invention.

The present invention relates to an improved warming unit for warming a patient infusion medium, such as prior to introducing the medium into a patient's body. Referring to FIG. 1, in one embodiment, the warming unit 10 forms part of an infusion medium warming system, which further includes a power supply 20, a controller 30, a reservoir 35 connected to the warming unit 10, and a coupling 40 extending between the controller 30 and the warming unit 10. In the embodiment of FIG. 1, the controller 30 controls power delivery to, transmits data to, and receives data from the warming unit 10, such as temperature data.

The controller 30 includes, for example, a display for displaying information, such as a visual alarm, and/or a temperature of the medium flowing through the warming unit 10 (e.g., inlet and/or outlet temperature). According to one embodiment, the controller 30 receives and displays a temperature of a heating element (described further below) of the warming unit 10. According to one embodiment, the controller 30 further includes an audible and/or visual alarm that is triggered when, for example, a monitored temperature exceeds a predetermined value or when another alarm condition exists.

The power supply 20 provides a regulated voltage to the controller 30 and/or to the warming unit 10. Although illustrated as two separate components, the power supply 20 may also be integral with the controller 30.

Figure 2:
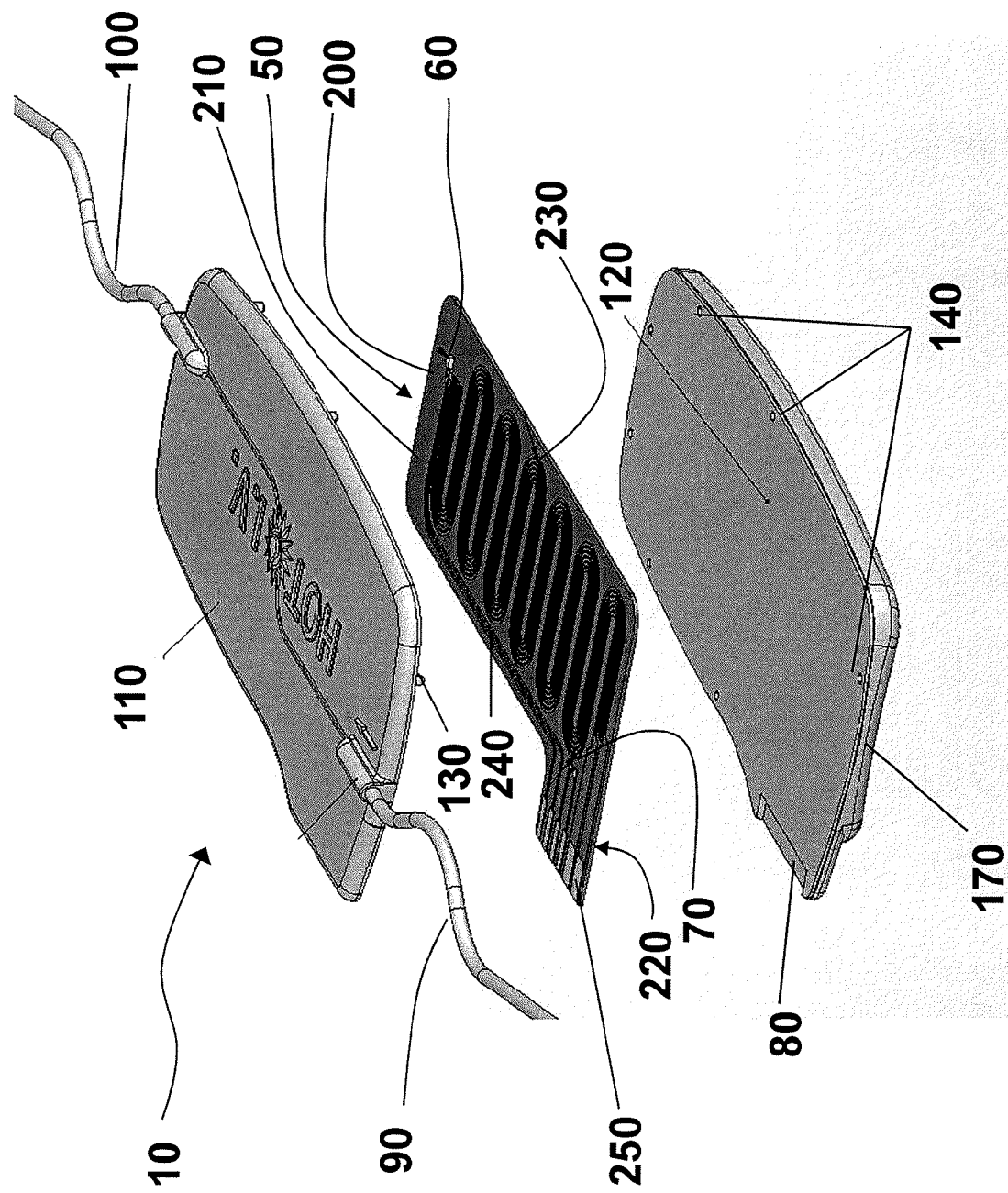
FIG. 2 shows an exploded view of the warming unit according to an embodiment of the present invention.
Figure 3:
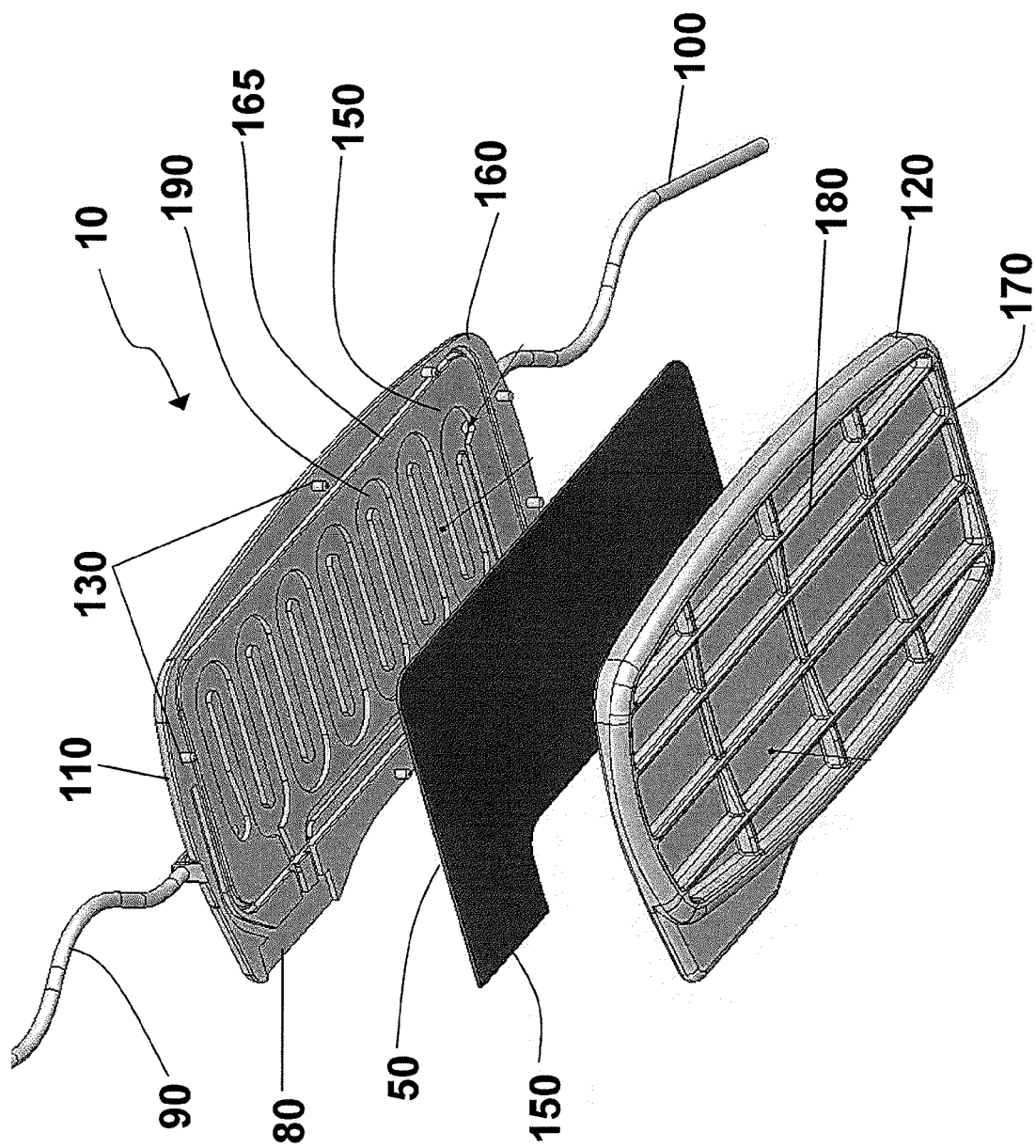
FIG. 3 shows another exploded view of the warming unit of FIG. 2.

Referring to FIGS. 2 and 3, according to one embodiment of the present invention, the warming unit 10 includes outer casing portions 110, 120, a laminated heating assembly 50, first and second sensors 60 and 70, a connector port 80, an inlet tube 90, and an outlet tube 100.

Figure 4A:
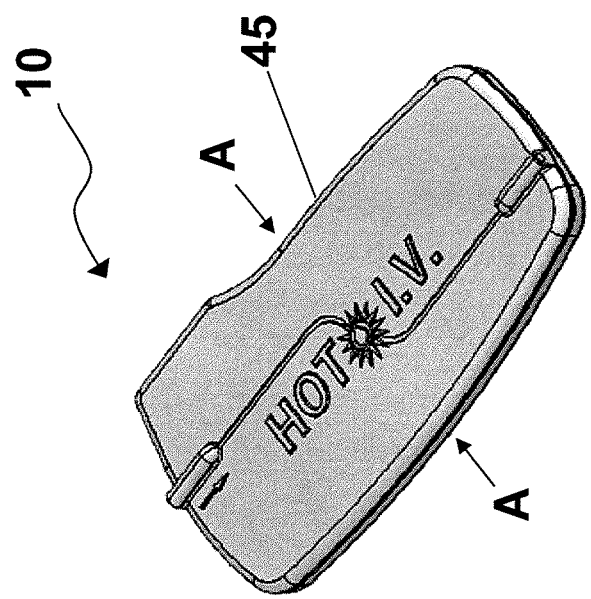
FIG. 4A is a perspective view of a central portion of the warming unit, in accordance with an embodiment of the present invention.
Figure 4B:
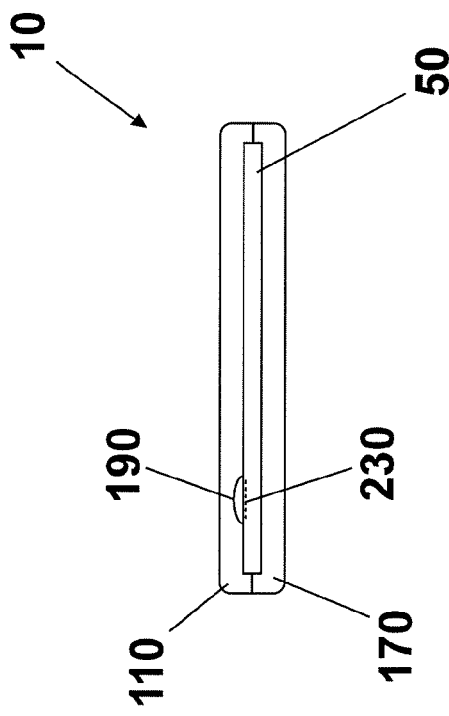
FIG. 4B is a cross-sectional view of a first variation of the warming unit of FIG. 4A.
Figure 4C:
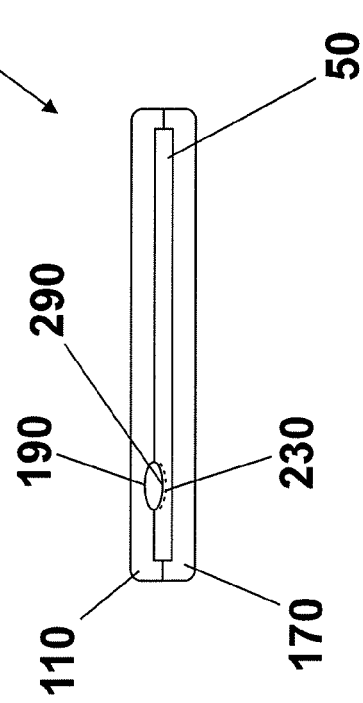
FIG. 4C is a cross-sectional view of a second variation of the warming unit of FIG. 4A.
Figure 5:
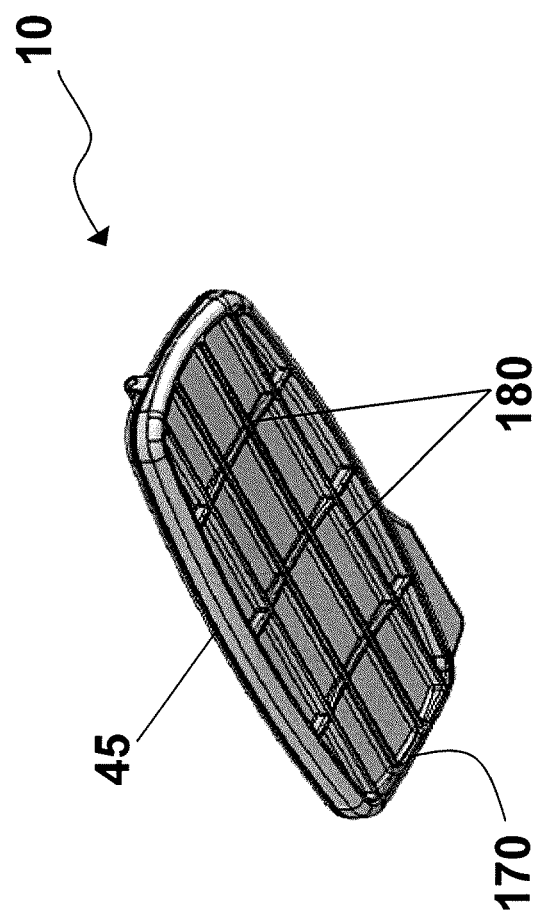
FIG. 5 is another perspective view of the warming unit of FIG. 4.

The first casing portion 110 and second casing portion 120, upon assembly, form a single enclosing casing (see assembled casing 45 of FIGS. 4 and 5). In one embodiment, the first and second casing portions 110, 120 are formed from a polymeric material using an injection molding process, although it is within the scope of the present invention to use any suitable material and any suitable method to form the casing portions 110, 120. An inner surface of the first casing portion 110 may include a plurality of extensions 130 distributed along a perimeter thereof. The extensions 130 engage corresponding openings 140 formed in the second casing portion 120, for example. The extensions 130 and the corresponding openings 140 perform a positioning and union function to align and connect the first and second casing portions 110, 120, upon assembly. However, it is within the scope of the invention to include alternate structure, such as a raised ridge and corresponding mating groove or other features to align and connect the first and second casing portions 110, 120. In one embodiment, the extensions 130 and the corresponding openings 140 are integrally formed in the respective first and second casing portions 110, 120.

Referring to FIG. 3, in one embodiment, the inner surface of the first casing portion 110 further includes a recess 150 for retaining the laminated heating assembly 50 therein. According to one embodiment, the depth of the recess 150 matches the thickness of the laminated heating assembly 50 so that, when the laminated heating assembly 50 is inserted into the recess 150, a surface thereof, opposite the first casing portion 110, is approximately flush with a raised edge portion 160 of the first casing portion 110 surrounding the recess 150. Therefore, once the warming unit 10 is assembled, adjacent inner faces of the first and second casing portion 110, 120 abut each other without forming a gap or by formulating a minimal gap therebetween.

According to one embodiment, the warming unit 10 also includes a seal, which seats into the groove 165 formed in the first casing portion 110 along the perimeter of the recess 150. The seal, such as an o-ring or gasket, provides the casing 45 with a seal at the interface between the first and second casing portions 110, 120. In some embodiments, once assembled, the first and second casing portions 110, 120 are permanently secured to each other, such as by ultrasonic welding, gluing, or any other suitable method of attachment.

Control circuitry for controlling a temperature of the medium flowing through the warming unit 10, for example, is external to the warming unit 10 and is contained, for example, in the controller 30, as shown in FIG. 1. Consequently, the warming unit 10 is not susceptible to shorting, smoking, or catching fire, as may be caused, for example, by escaped medium contacting the control circuitry, as could have occurred in prior art devices in which the control circuitry was integral with the warmer. As a result, in contrast to the prior art, the warming unit 10 of the present invention provides improved patient and caregiver safety and reliability.

As best shown in FIG. 3, in one embodiment the second casing portion 120 includes an outer concave surface 170 having a plurality of criss-crossing ribs 180. The ribs 180 of this embodiment form a grid pattern, for example, in the concave surface 170. The concave surface 170 is able to conform to a portion of a patient's anatomy, for example, such as an arm or leg, and, thus position the warming unit 10 in a stable manner when in use. The plurality of ribs 180 allow an air gap to exist between the patient and the warming unit 10 and thereby reduce the surface area of the concave surface 170 in contact with the patient's anatomy. As a result, the amount of heat transferred from the warming unit 10 to the patient is reduced, increasing the patient's comfort level when the warming unit 10 is operating. In addition, the ribs 180 generally increase rigidity of the unit 10.

As further shown in FIG. 3, the inner surface of the first casing portion 110 defines a first portion of a fluid conduit 190 extending within the warming unit 10. According to one embodiment, this portion of the fluid conduit 190 defines a serpentine or meandering path, prolonging a time period (via increased path length of medium travel) during which a medium passing therethrough is in contact with, or located in close proximity to, the laminated heating assembly 50, versus a non-serpentine path.

As best shown in FIG. 2 and the cross-sectional views of FIGS. 4B and 4C, in some embodiments, the laminated heating assembly 50 includes a plate or other substrate 200 sandwiched between first and second insulating sheets 210, 220, with a heating element 230 being located in or on the substrate 200. The surface of the laminated heating assembly 50 facing the first casing portion 110 abuts the fluid conduit portion 190 of the casing portion, so as to form an enclosed conduit upon assembly. Alternatively, a fluid conduit portion 290 is also formed on the heating assembly 50 corresponding to the fluid conduit 190 of the casing portion 110. The conduit of some embodiments of the present invention is formed with sizing and/or shaping of the cross-sectional area of the conduit such that air bubbles are unlikely to form in the medium to be conducted.

The reduced likelihood of bubble formation in the conduit results from the physics of bubbles. In general, the surface tension of a fluid determines the necessary wall tension for formation of bubbles, and bubbles generally form in spherical shapes due to the need for wall tension to be minimized over the entire surface of the bubble. The pressure difference between the air inside and the fluid outside of a bubble depends on the surface tension of the fluid and the radius of the bubble, according to the following equation:

$$P_i - P_o = 4T/r$$

where $P_i$ is the pressure of air inside the bubble, $P_o$ is the pressure of the fluid outside the bubble, T is the surface tension, and r is the radius of the bubble. See, e.g., http://hyperphysics.phy-astr.gsu.edu/hbase/surten2.html, as viewed on Aug. 2, 2006, the entirety of which is incorporated herein by reference. Thus, generally, as r becomes very small (e.g., as must occur in a small cross-sectional conduit), and as T is generally constant, the pressure difference so as to form a bubble becomes increasingly larger, thereby correspondingly reducing the likelihood that a bubble can form.

In embodiments of the present invention, the heating element 230 extends adjacent or in close proximity to the fluid conduit 290, upon assembly. However, the shape of the heating element 230 is not so limited to the example shown in FIG. 2, and it is within the scope of the present invention for the heating element 230 to form any shape within the warming unit 10, such as a series of approximately parallel line portions, a criss-crossing grid pattern, or a spiral pattern. The heating element 230 may be formed from any suitable material, such as a metal, metal alloy, a ceramic, or any material that may provide heating such as by passing an electrical current therethrough.

According to one embodiment, first and second sensors 60, 70 are attached to the laminated heating assembly 50. As shown in FIG. 2, the first sensor 60 is disposed within the fluid conduit 190 near the outlet tube 100, although the first sensor 60 may be disposed anywhere within or near the fluid conduit 190 (FIG. 3) to measure medium or other fluid temperature at the point the sensor 60 is located. In one embodiment, the first sensor 60 is disposed within or near the outlet tube 90 (FIG. 3) and within or near the fluid conduit 190 (FIG. 3), and measures the outlet temperature of the medium (or other fluid) passing through the warming unit 10, for example. The second sensor 70, as shown in FIG. 2, is disposed near an end of the warming unit 10, such as near the inlet tube 90 (FIG. 3), although the second sensor 70 may be located at any location adjacent to or near the heating element 230, for example, to measure the temperature of the heating element 230. Examples of sensors applicable to the present invention include, but are not limited to, thermocouples, thermistors, resistor elements, and any other suitable device for measuring or otherwise determining temperature.

While FIG. 2 illustrates an embodiment of the warming unit 10 having only two sensors, it is within the scope of the present invention that the warming unit 10 include a single temperature sensor or that the warming unit 10 include temperature sensors in excess of two. Moreover, the temperature measuring function may be performed by other methods and hardware than the sensors 60, 70, such as by measuring the power applied to the heating element 230. Thus, the heating element 230 may be used to perform both a warming function and a temperature sensing function, permitting the elimination of a dedicated temperature measuring sensor.

It is also within the scope of the present invention that the warming unit 10 include other features, such as a flowrate measurement device and/or medium leakage detection features. The flowrate measurement device measures a flowrate of a medium passing through the warming unit 10 or the total amount of a medium delivered to a patient through the warming unit 10 over a specified period of time, for example. The leakage detection features detect the presence of leakage conditions, such as the presence of moisture outside the conduit path.

In one embodiment, circuit paths 240 for the first and second sensors 60, 70 and the heating element 230 extend from the respective devices to a connector portion 250 of the laminated heating assembly 50. In one embodiment, the circuit paths 240 are formed using printed circuit board manufacturing methods. Alternately, for example, the circuit paths 240 comprise a plurality of wires or other couplings.

The exemplary warming unit 10 of FIG. 2 includes six circuit path portions 240, wherein one pair of circuit paths 240 extend from each of the first and second sensor 60, 70, and a pair of circuit paths 240 extend from the heating element 230. Each circuit path 240 terminates at the connector portion 250.

A connector 40 engages the connector portion 250 to provide power to the heating element 230 and to transmit signals between the first and second sensors 60, 70 and the controller 30. While the connector 40 is illustrated as mating with a six-pin connector portion 250, it is within the scope of the present invention for the connector 40 to be connectable to any appropriate number of pins. For example, a warming unit 10 with more devices (e.g., additional sensors or a flowrate measurement device) may include an increased number of pins. Accordingly, a connector 40 with an increased number of pin connections may be required. Conversely, a warming unit 10 with fewer devices requires fewer corresponding pins. In one embodiment, the connector 40 is detachable from the warming unit 10, allowing the warming unit 10 to be easily disconnected from the controller 30. Among other things, use of such a detachable connector provides flexibility in portability of the warming unit and allows the use of a variety of power sources (e.g., any power source meeting the power requirements may be connected via the connector portion 250, so long as suitable connection mechanism for mating with the connector portion 250 is provided). Once detached, the warming unit 10 may be discarded or otherwise removed, for example, and a new warming unit 10 may be attached to the connector 40. The warming unit 10 may also be permanently connected to the controller 30 or power supply 20, such as by soldered or otherwise permanently attached coupling, rather than via a detachable connector 40.

As further shown in FIGS. 2 and 3, the inlet tube 90 and the outlet tube 100 are attached within respective openings in the casing portion 110 of the warming unit 10 and, for example, may be permanently attached. An embodiment of the warming unit 10 in which the inlet and outlet tubes 90, 100 are permanently attached significantly reduces or eliminates risk of leakage at the interface of the inlet and outlet tubes 90, 100 with the casing portion 110 of the fluid warmer 10 relative to prior art detachable tubes. In one embodiment, the inlet tube 90 comprises flexible intravenous tubing. The inlet tube 90 and outlet tube 100 may also integrally or detachably include any intravenous tubing fittings and/or related features, such as a male or female luer, a three-way stopcock, a Y-site connector (also referred to herein as "Y-fitting"), a slide thumb wheel, a slide pitch plate, a check valve, and/or a needleless injection site luer.

A Y-fitting or three-way stopcock included with the input tube 90 is useable, for example, for introducing a second medium that is also to be warmed, since the second medium will pass through the warming unit 10 with a first warmed medium prior to entering the patient's body. Conversely, a Y-fitting or three-way stopcock included with the output tube 100 is usable for introducing a second medium, for which passage through the warming unit 10 is not desired. For example, oncology drugs for which effectiveness is altered by heat may be introduced at a position downstream from the warming unit 10 to prevent inappropriate or harmful warming from adversely affecting the drugs. Additionally, the inlet tube 90 and outlet tube 100 may also include features for acceptance of a needle, spike, or catheter, for example, particularly within or proximate to the outlet tube 100. It is within the scope of the invention to include any intravenous tubing fitting or other feature usable with standard intravenous tubing applications.

FIG. 4A is a perspective view of a central portion of the warming unit, in accordance with an embodiment of the present invention.

FIG. 5 is another perspective view of the warming unit of FIG. 4A.

Figure 6:
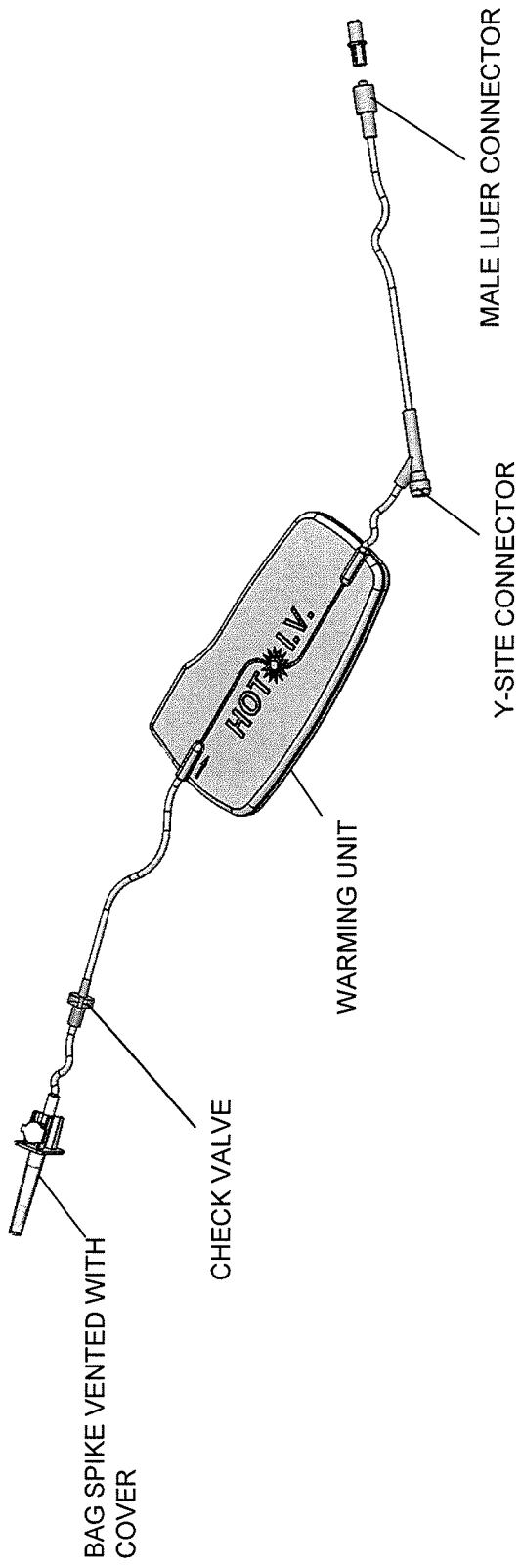
FIG. 6 shows an embodiment of the warming unit having various intravenous fittings included therewith.

An example embodiment of the warming unit including various types of intravenous fittings is illustrated in FIG. 6.

Figure 7:
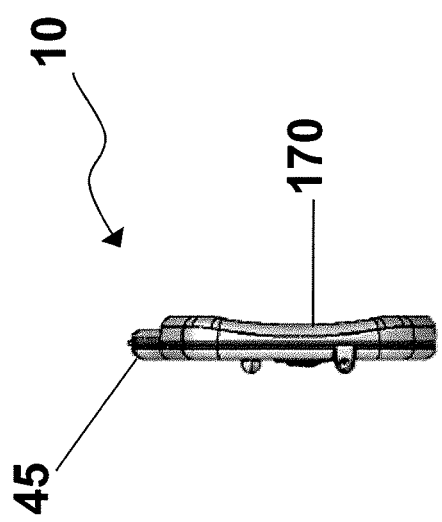
FIG. 7 is a side view of a warming unit according to an embodiment of the present invention.

FIG. 7 is a side view of a warming unit according to an embodiment of the present invention.

While there has been described what are at present considered to be preferred embodiments of the present invention, it will be understood that various modifications may be made thereto. All such modifications are considered to fall within the true spirit and scope of the invention. Other modifications will be apparent to those skilled in the art.

The invention claimed is:

1. A warming unit for warming a patient infusion medium comprising:
   an inlet tube;
   an outlet tube;
   a fluid conduit disposed between and in communication with the inlet tube and the outlet tube;
   a heater disposed proximate to the fluid conduit for warming the patient infusion medium; and
   an outer casing sealably enclosing the fluid conduit and housing the heater, wherein at least a portion of the fluid conduit is defined by an inner surface of the outer casing.

2. The warming unit according to claim 1, wherein the inlet tube and the outlet tube are permanently attached to the outer casing.

3. The warming unit according to claim 1, the heater comprising:
   a substrate; and
   a heating element disposed on the substrate.

4. The warming unit according to claim 3,
   wherein the fluid conduit forms a serpentine path;
   wherein the heating element forms a shape corresponding to the serpentine path of the fluid conduit; and
   wherein the shape of the heating element and the path of the fluid conduit generally align.

5. The warming unit according to claim 1, further comprising:
   a connector that couples the warming unit to a separate controller that is located externally to the outer casing of the warming unit.

6. The warming unit according to claim 1, further comprising:
   a sensor for measuring a temperature of the patient infusion medium passing through the warming unit.

7. The warming unit according to claim 6, wherein the sensor is disposed within the fluid conduit.

8. The warming unit according to claim 1, wherein a portion of the fluid conduit is defined by the heater.

9. The warming unit according to claim 1, wherein a portion of the outer casing is contoured to conform to an anatomical shape of a patient.

10. The warming unit according to claim 9, wherein the contoured portion outer casing is configured to provide an air gap between a portion of the outer casing and a patient.

11. The warming unit according to claim 1, wherein the warming unit is disposable.

12. The warming unit according to claim 1, wherein the outer casing comprises:
   a first casing portion; and
   a second casing portion,
   wherein the first and second casing portions are permanently attachable to each other.

13. The warming unit according to claim 12, further comprising: a seal disposed between the first and second casing portions.

14. The warming unit according to claim 1, wherein the heater comprises
   a laminated heating assembly, the assembly including:
      a first insulating sheet;
      a second insulating sheet;
      a substrate disposed between the first and second insulating sheets;
      a heating element disposed on the substrate, wherein a portion of the fluid conduit is defined by the laminated heating assembly;
      a sensor disposed on the substrate; and
      a plurality of electrical circuit paths coupled to the heating element and the sensor.

15. The warming unit according to claim 14, wherein the plurality of circuit paths extend to the connector.

16. The warming unit according to claim 14, wherein the plurality of circuit paths are formed on the substrate.

17. The warming unit according to claim 14, wherein the fluid conduit forms a serpentine path;
   wherein the heating element forms a shape corresponding to the serpentine path of the fluid conduit; and
   wherein the shape of the heating element and the path of the fluid conduit generally align.

18. A system for delivering and warming a patient infusion medium comprising:
   a warming unit, the warming unit including:
      an inlet tube;
      an outlet tube;
      a fluid conduit disposed between and in communication with the inlet tube and the outlet tube;
      a heating element disposed proximate to the fluid conduit for warming the patient infusion medium, wherein a portion of the fluid conduit is defined by the heating element; and
      an outer casing enclosing the fluid conduit and the heating member, wherein at least a portion of the fluid conduit is defined by an inner surface of the outer casing;
   a controller provided outside the outer casing for controlling an operation of the warming unit; and
   a power supply for providing power to the warming unit.

19. The system according to claim 18, further comprising: a reservoir connected to the warming unit.

20. The system according to claim 18, wherein the fluid conduit forms a serpentine path;
   wherein the heating element forms a shape corresponding to the serpentine path of the fluid conduit; and
   wherein the shape of the heating element and the path of the fluid conduit generally align.

21. The system according to claim 18, the warming unit further comprising:
   a connector portion for coupling the warming unit to the controller.

22. The system according to claim 18, further comprising:
   a fitting coupled to the outlet tube;
   wherein a second patient infusion medium is introduced to the outlet tube via the fitting.

23. The system according to claim 22, wherein the second patient infusion medium is introduced via the fitting so as to avoid adverse heating effects on the second patient infusion media.

24. The system according to claim 22, wherein the second patient infusion medium includes an oncology drug.

* * * * *